(12) United States Patent
Mercer

(10) Patent No.: US 8,605,285 B2
(45) Date of Patent: Dec. 10, 2013

(54) APPARATUS AND METHOD FOR SAMPLE ANALYSIS

(76) Inventor: Ian Petar Mercer, Dublin (IE)

( * ) Notice: Subject to any disclaimer, the term of this patent is extended or adjusted under 35 U.S.C. 154(b) by 346 days.

(21) Appl. No.: 12/990,221

(22) PCT Filed: Jun. 1, 2009

(86) PCT No.: PCT/GB2009/050600
§ 371 (c)(1),
(2), (4) Date: Oct. 29, 2010

(87) PCT Pub. No.: WO2009/147425
PCT Pub. Date: Dec. 10, 2009

(65) Prior Publication Data
US 2011/0075150 A1  Mar. 31, 2011

(30) Foreign Application Priority Data

Jun. 2, 2008 (GB) .................................... 0809894.9
Oct. 2, 2008 (GB) .................................... 0817984.8
Feb. 5, 2009 (GB) .................................... 0901778.1

(51) Int. Cl.
*G01B 9/02* (2006.01)
*G01B 11/02* (2006.01)

(52) U.S. Cl.
USPC ............ 356/451; 356/479; 356/497; 356/521

(58) Field of Classification Search
USPC ......................................................... 356/521
See application file for complete search history.

(56) References Cited

U.S. PATENT DOCUMENTS 7,355,716 B2 * 4/2008 de Boer et al. ................ 356/479
2006/0263777 A1 * 11/2006 Tong ................................. 435/6
2008/0258071 A1 * 10/2008 Arnold et al. ................ 250/373

* cited by examiner

*Primary Examiner* — Tarifur Chowdhury
*Assistant Examiner* — Sunghee Y Gray

(57) ABSTRACT

Prior art coherent optical wave mixing has permitted two-dimensional maps from which coupled quantum transitions have been identified in molecular samples. However, extended signal accumulation times and computer processing are required for a detailed molecular analysis, which can lead to sample toxicity and difficulties in interpretation. These and other requirements are reduced by an apparatus arranged for the projection of an image that directly encodes quantum couplings from a sample. Such an apparatus includes a source component 36, a diffractive optical component 25 for generating at least three light fields 1, 2, 3 from one light field 23, one or more optical telescopes 26 and 27 wherein the transverse separation between optical paths is modified from that possible to define with a single telescope between common object and image points, a sample 11 containing said image point, and a means for resolving and detecting the angular variation of light emission from a sample. The occurrence of coupled quantum transitions or energy transfers are identified providing a means for sample analysis thereby.

19 Claims, 8 Drawing Sheets

FIGURE 1
Figure 1(a)
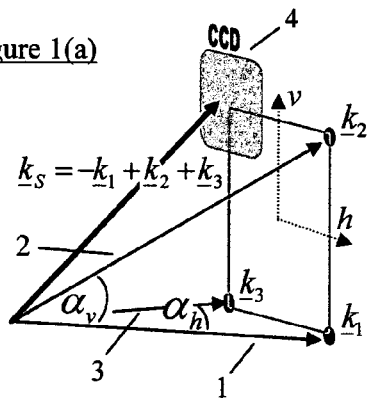
Figure 1(b)
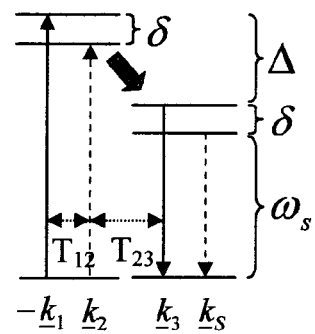
Figure 1(c)
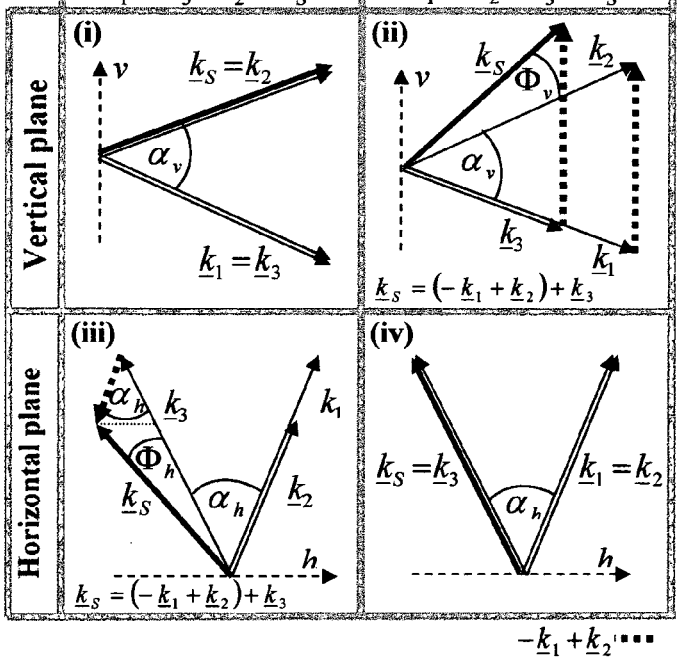
Figure 1(d)
Mapping at CCD
$\Phi_v = \alpha_v \dfrac{\Delta}{\omega_S}$
$\Phi_h = \alpha_h \dfrac{\delta}{\omega_S}$

FIGURE 2
Figure 2(a)
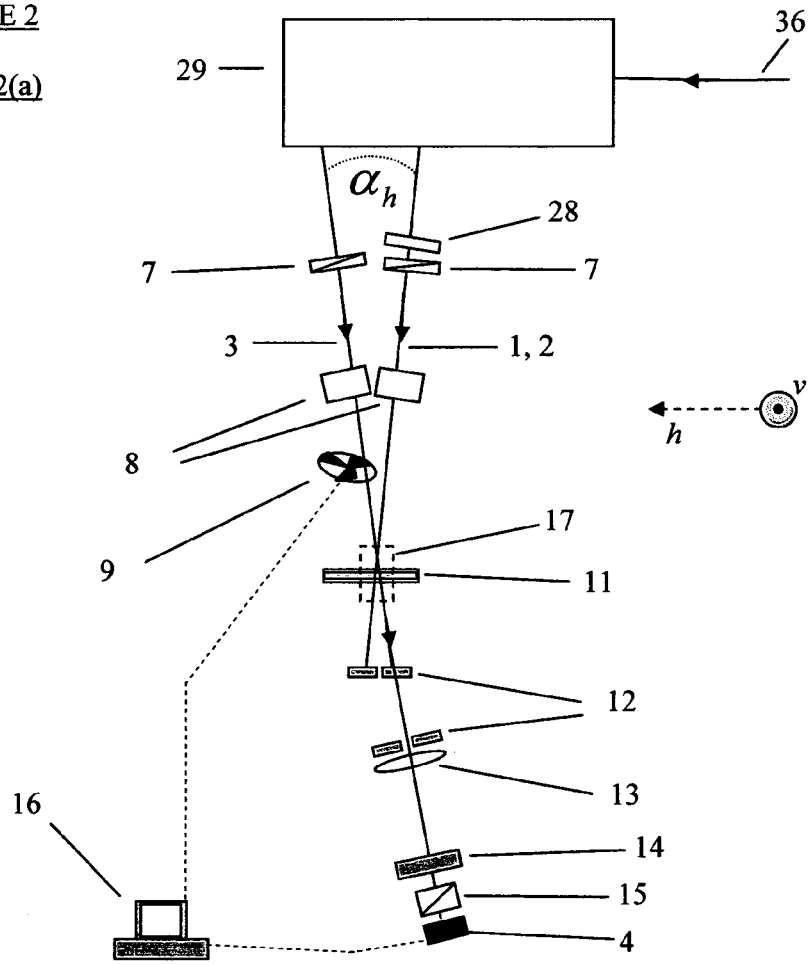
Figure 2(b)
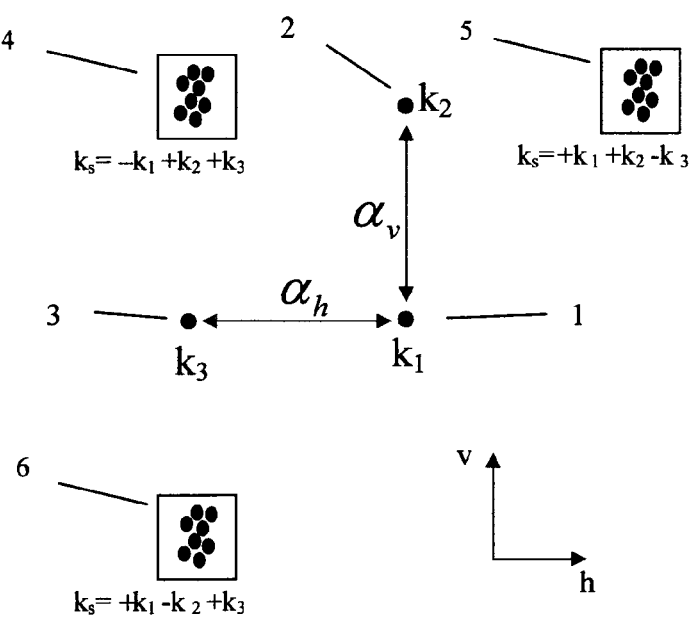

FIGURE 3
Figure 3(a)
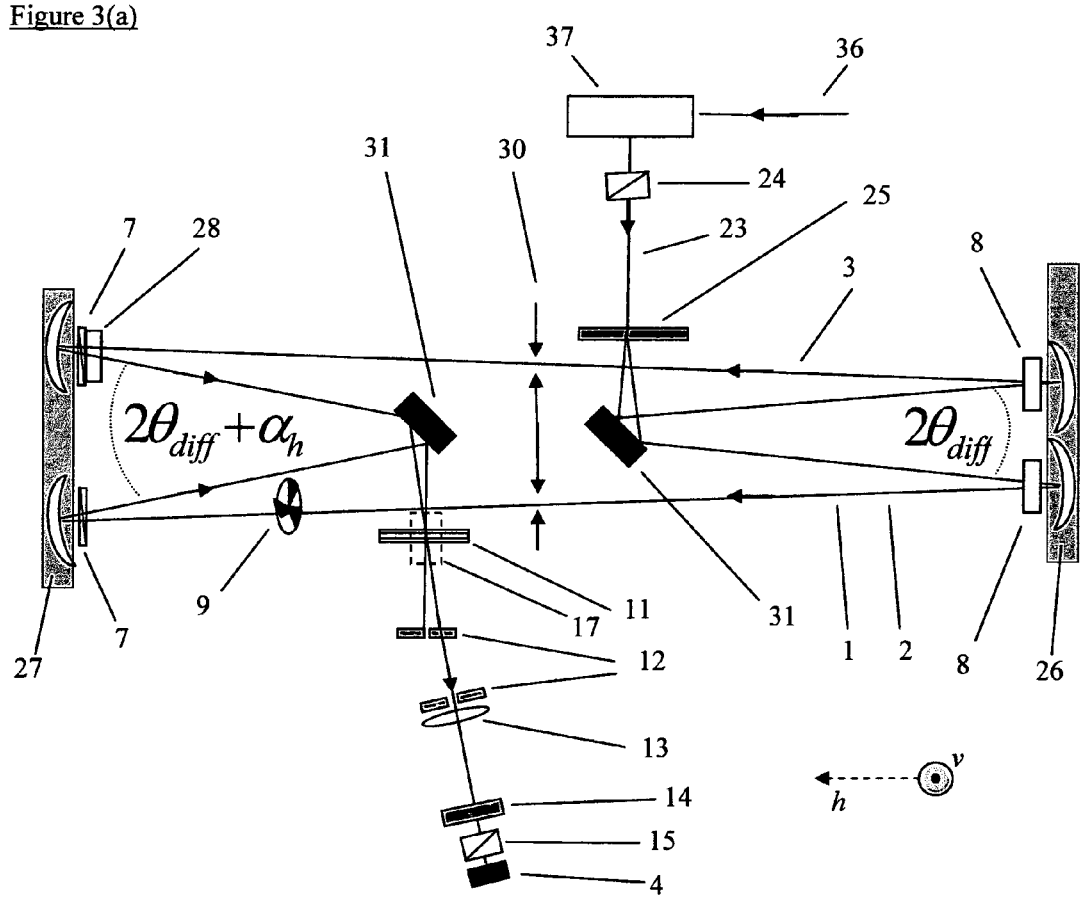
Figure 3(b)
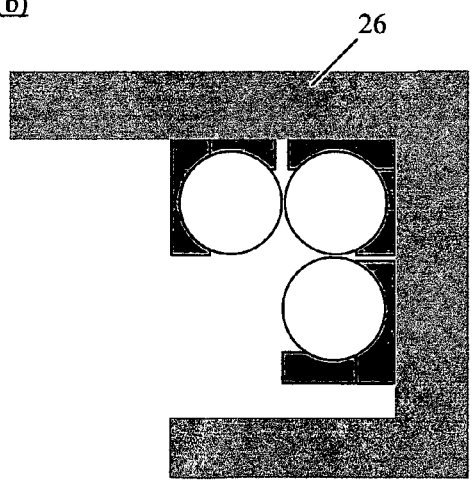

FIGURE 4
Figure 4(a)
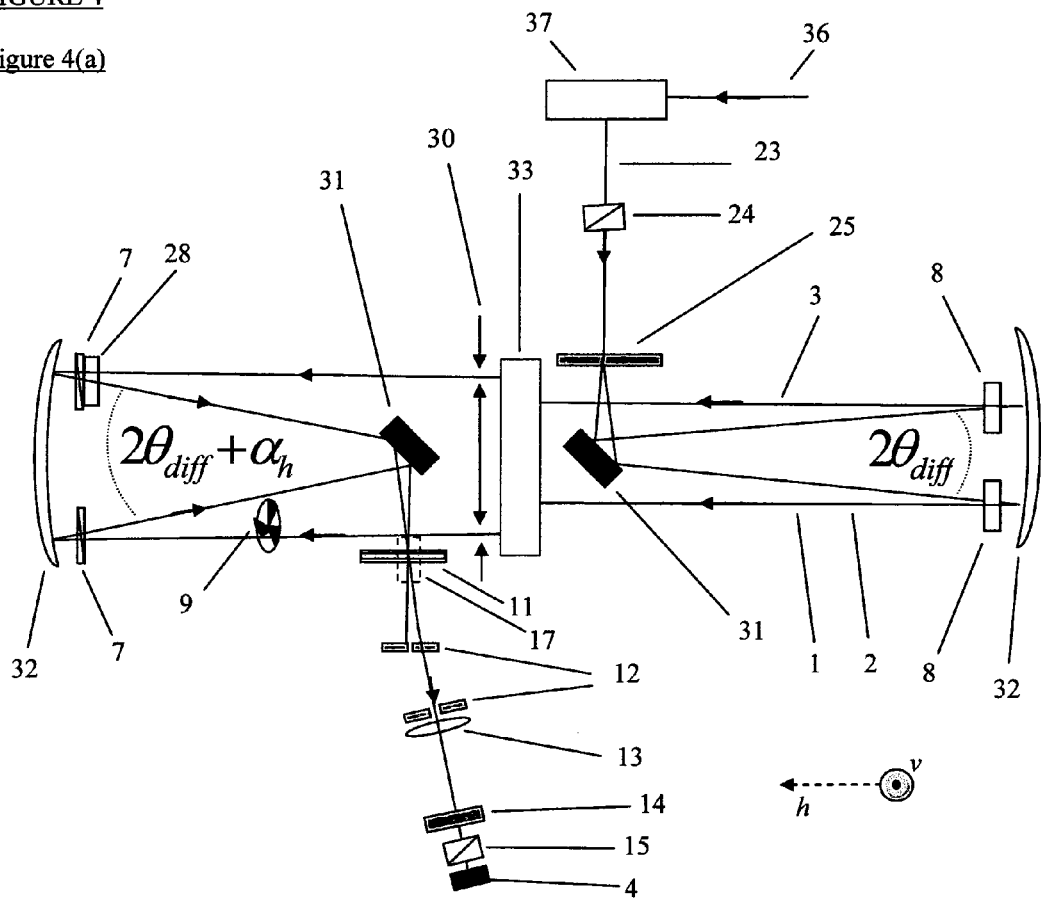
Figure 4(b)
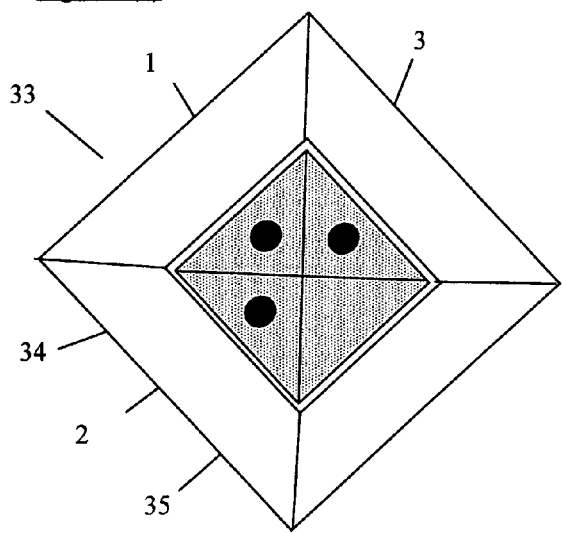
Figure 4(c)
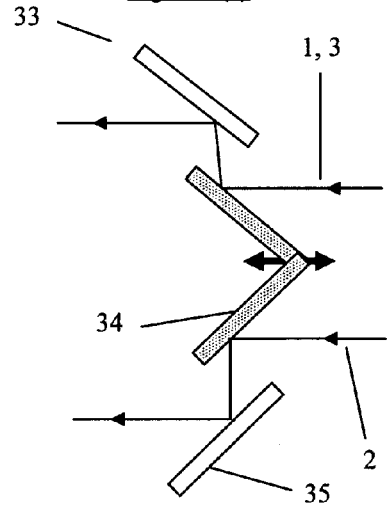

FIGURE 5
Figure 5(a)
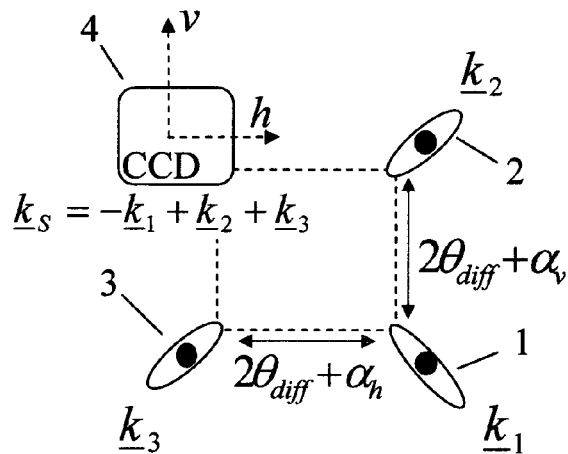
Figure 5(b)
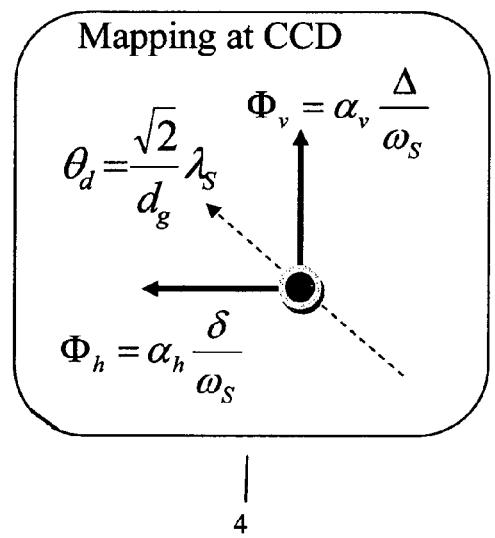
Figure 5(c)
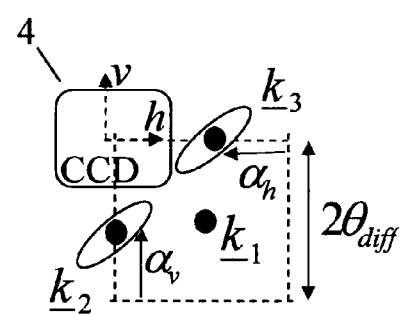
Figure 5(d)
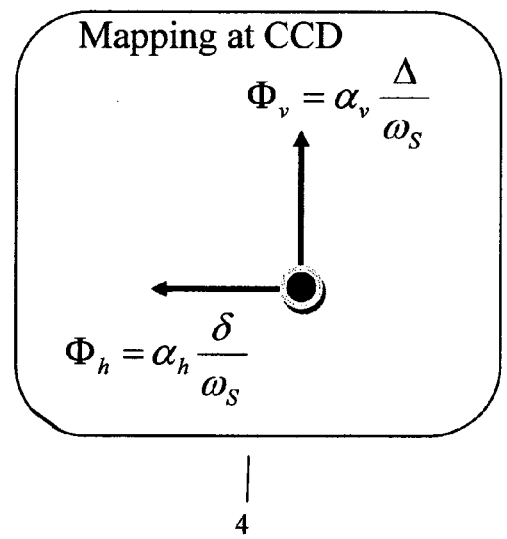

FIGURE 6
Figure 6(a)
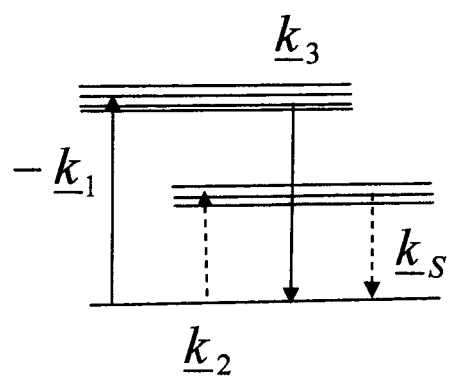
Figure 6(b)
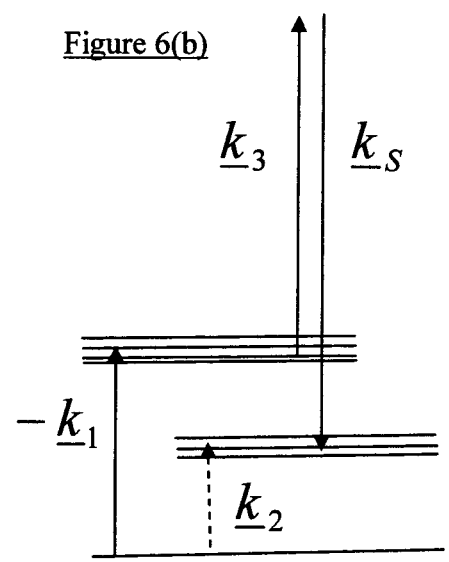

FIGURE 7
Figure 7(a)
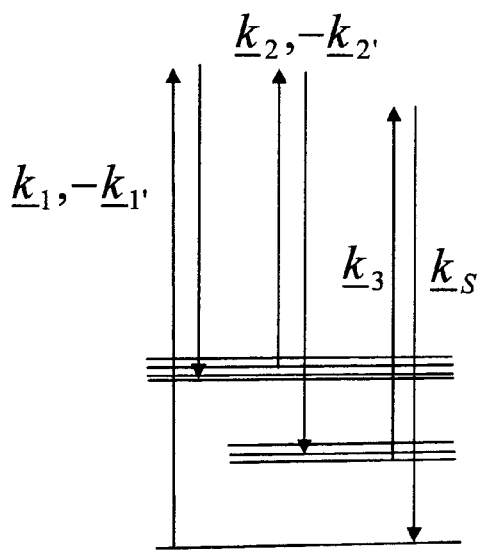
Figure 7(b)
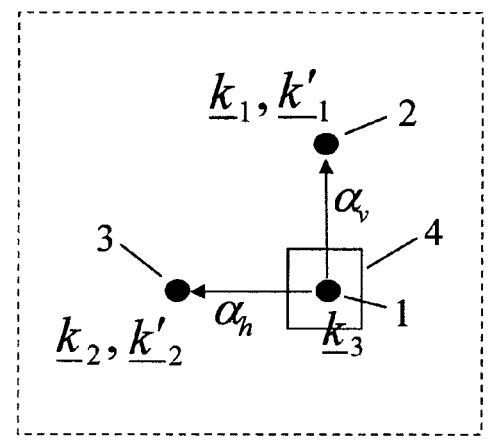
$$k_S = (\underline{k}_1 - \underline{k}_{1'}) + (\underline{k}_2 - \underline{k}_{2'}) + \underline{k}_3$$
or $\underline{k}_S = \underline{\Delta k}_1 + \underline{\Delta k}_2 + \underline{k}_3$
Figure 7(c)
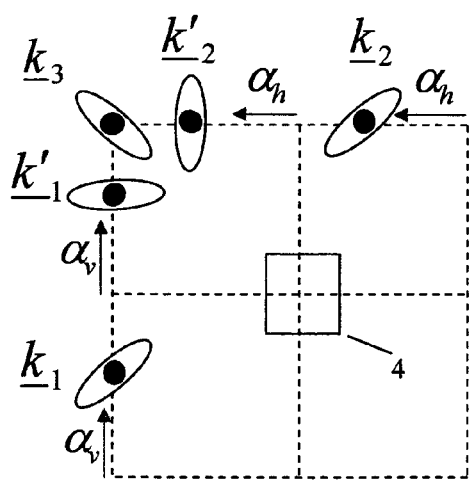
$$\underline{k}_S = (\underline{k}_1 - \underline{k}_{1'}) + (\underline{k}_2 - \underline{k}_{2'}) + \underline{k}_3$$
Figure 7(d)
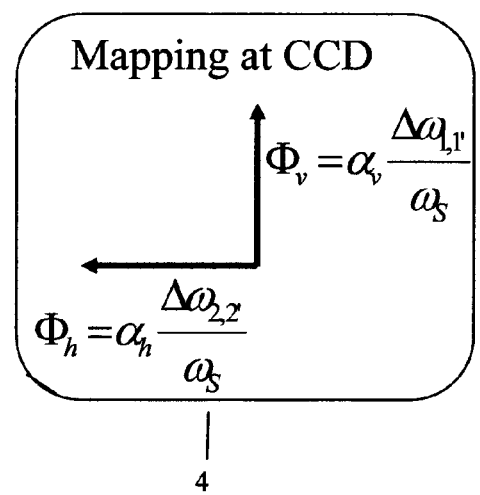

FIGURE 8
Figure 8(a)
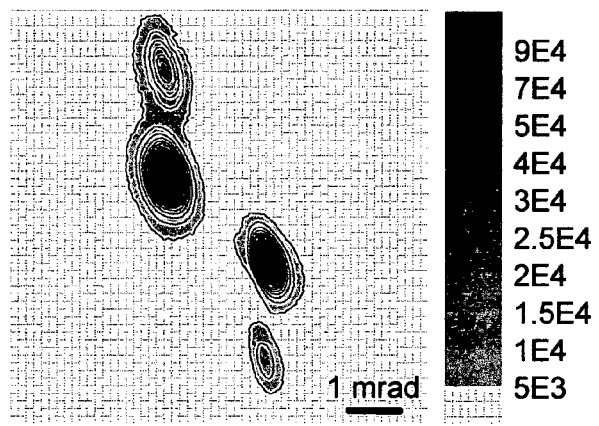
Figure 8(b)
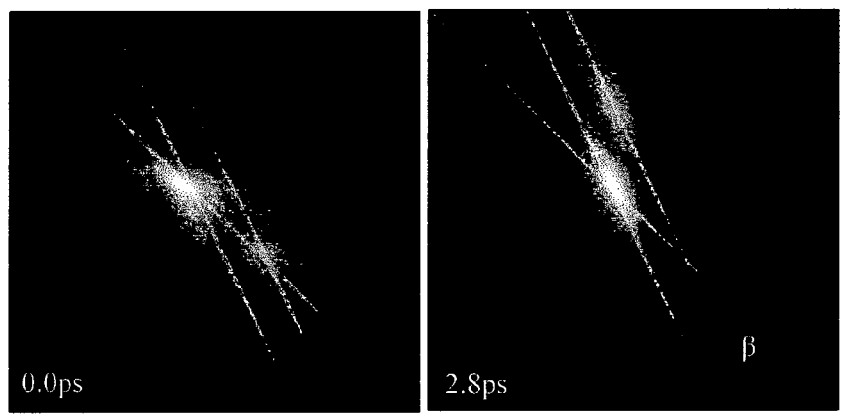
Figure 8(c)
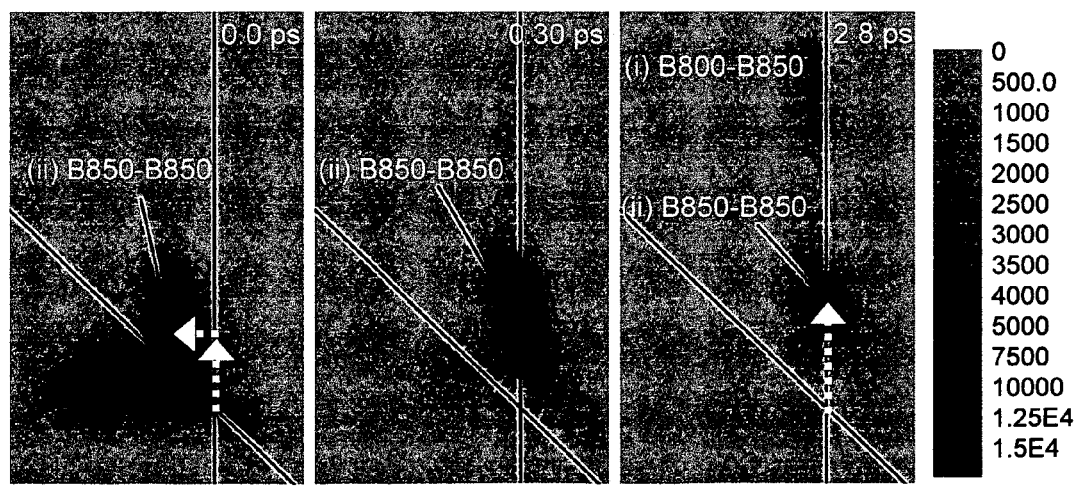

APPARATUS AND METHOD FOR SAMPLE ANALYSIS

The present invention relates to a means and method for an improvement over prior art coherent laser-optical wave-mixing arrangements for the sensing of either the molecular composition, structure or function of a sample. More particularly, this invention relates to an optical apparatus and method for the direction of light to a molecular sample and the direction of light from said sample to a detector. Molecular analysis is by means of resolving the angular variation of light emission from a molecular sample, wherein a two-dimensionally detected light distribution encodes coherently coupled quantum transitions or energy transfers occurring within the sample.

Methods of coherent optical four wave-mixing use multiple laser beams containing light pulses of variable delay directed to spatially overlap at a sample (S. Mukamel, *Principles of nonlinear optical spectroscopy*, Oxford University Press, 1995). These methods have been widely used to obtain information on sample molecular composition, structure or chemical function. However, the interpretation of these measurements is difficult in particular where quantum-optical transitions—absorbing in the ultra-violet, visible or infra-red—are strongly coupled. In order to better determine either the molecular composition, structure or chemical function of a sample, new methods are required that can reveal details of quantum couplings within a sample, for example to distinguish between energy transfers and coherent couplings between electronic quantum transitions within the sample. Significant progress has been made recently with the extension of the photon echo four wave-mixing method to deliver two-dimensional maps via heterodyned detection. This has been applied to systems ranging from small molecules (J. D. Hybl, A. A. Ferro, and D. M. Jonas, J Chem Phys 115, 6606, 2001) to semiconductors (X. Li et al., Physics Review Letters 96, 057406, 2006 and; T. Zhang et al., Proceedings of the National Academy of Sciences of the United States of America 104, 14227, 2007) and biological molecules (S. Kim at al, J Phys Chem B 112, 10054, 2008 and; C. Fang at al., P Natl Acad Sci USA 105, 1472, 2008) and has recently provided strong evidence of a quantum beating between coherently coupled electronic transitions molecules in a photosynthetic system (G. S. Engel et al., Nature 446, 782, 2007). Prior to the present invention, the above heterodyned method provides information on coherent couplings between quantum (electronic or vibrational) transitions in which a coherent coupling of electronic quantum transitions is predicted to give a synchronised modulation of feature amplitudes and widths for multiple maps recorded as a function of an optical delay times (A. V. Pisliakov, T. Mancal, and G. R. Fleming, Journal of Chemical Physics 124, 2006).

A problem with the above prior art heterodyned method and for methods that are sensitive to quantum coherence (such as a three pulse photon echo peak shift method) and details of quantum couplings (such as with a six wave-mixing method), is that long signal accumulation times are required, typically ranging from minutes to hours to deliver a two-dimensional data set. This results from a requirement for fine-step scanning of one or more time delays between optical pulses and generally from a requirement for signal averaging to separate a weak signal from competing background emission. Long exposure times can lead to a disadvantageous photo-degradation and toxicity for sensitive samples. To circumvent this, samples may be flowed, however this requires a large sample volume at high flow rate which is disadvantageous for use with samples of high value or samples available in small quantities. Laser pulse repetition rates with such prior art methods are typically in the range of 1 kHz to 100 MHz and whilst an increase in repetition rate can lead to a decrease in the data accumulation time, it disadvantageously increases the thermal loading in the sample and the rate of sample photo-degradation.

Another problem with the above prior art heterodyned method is a requirement for integral transform (Fourier) post-processing. In current heterodyned two-dimensional approaches, different interaction energies that contribute to a common emission energy are summed at a single detector, to be subsequently separated by a Fourier transform in post processing. The dynamic range of the detector in such an arrangement therefore serves to limit the detection of weaker signals. Further, compensation of detected background light through integral transform processing can result in alterations to the shapes of low intensity features (T. Brixner, T. Mancal, I. V. Stiopkin et al., *Journal of Chemical Physics* 121 (9), 4221, 2004). This prior heterodyned method also requires a further disadvantageous computer processing and interpretation of multiple maps in order to quantify a coherent coupling between quantum transitions.

An object of the present invention is to provide a means for sample analysis. A further object is to provide for an instantaneous mapping distinguishing numerous coherent couplings between quantum transitions or distinguishing numerous energy transfers in a molecular sample. The present invention may be applied to characterise a sample via vibration transitions, molecular electronic transitions, molecular bonding transitions, or other quantum transitions. A further object of the present invention is to reduce the requirement for computational processing of data over that of the above prior art heterodyned wave-mixing scheme. A further object of the present invention is to directly distinguish coherently coupled quantum transitions from quantum energy transfers in a sample. A further object of the present invention is to distinguish weak signal emissions that are otherwise dominated by stronger emissions using prior wave-mixing methods. A further object of the present invention is to deduce the energies of quantum transitions for light-matter interaction pathways, measured simultaneously for numerous transitions. These and other objects of the invention will be apparent to those skilled in the art based on the teachings herein.

For methods that can distinguish quantum coherences, laser beams are arranged with waist sizes at the sample less than 100 times the laser wavelength. For example, waist sizes of less than 50 µm are common in four-wave-mixing for a light wavelength of 0.8 µm. This is advantageous for the generation of the light intensities required for efficient signal generation in nonlinear wave-mixing. In two-dimensional heterodyned four-wave-mixing with a broad bandwidth laser, a reduction in waist size (increasing the light divergence) further advantageously masks a variation in the angle of signal emission that will occur within the spatial profile of the heterodyning light beam. This variation in angle contributes to distortions in the two-dimensional maps, reducing the amount of information that can be retrieved (M. K. Yetzbacher et al., J Chem Phys 126, 2007). In contrast, the present invention, termed Angle-Resolved Coherent (ARC) wave-mixing herein, makes use of the angular distribution of the signal intensity and is advantaged by an increase in the light beam waist sizes at the sample.

By way of explanation, the direction of the signal emission in Angle-Resolved Coherent (ARC) four-wave-mixing is given by conservation of momentum as $\underline{k}_s = -\underline{k}_1 + \underline{k}_2 + \underline{k}_3$ for light field wave-vectors $\underline{k}_1, \underline{k}_2, \underline{k}_3$ and the generated signal $\underline{k}_s$ as is common in four-wave-mixing. Since the magnitude of each light-vector is frequency dependent, the direction of scattered light depends on the frequencies (energies) selected from each light field, which are governed by the behavior of the quantum transitions in the sample that interact with the light fields. The variation in the emission direction is however small. For example, for angles of 2° between light field optical paths at the sample in the horizontal and vertical planes respectively, a signal feature is deviated by only 0.01° for a difference in wavelength between light-sample interactions (for example between absorption and emission) of 5 nm at a wavelength of 800 nm. In order to provide sensitivity to this phenomenon, arrangements of the present invention are optimised with large light field waists at the sample, and arrangements are optimised for measuring the angular variation of signal emission.

The present invention advantageously provides information from a sample analysis that is difficult to deduce with the prior art heterodyned two-dimensional method. The parallel form of projection mapping in the present invention, without a requirement for the scanning of optical time delays to generate a map, permits: rapid sampling for an advantageous reduction in sample degradation or toxicity; an advantageous sensitivity to proteins in the native state; sensitivity to non-reversible chemical reactions; the ability to saturate or block strong signals (for example resulting from strong absorption features) for a preferential detection of weaker features and; a straight forward numerical subtraction of background light for an advantageous faithful representation of weak signal features. In one embodiment of the present intention, a quantum beat energy for coupled quantum transitions may be advantageously quantified without a requirement for any computer post-processing, as described by the teachings herein. The position of a discrete feature can map uniquely to each of the four light field interaction energies that produce the signal, this simultaneously for numerous quantum transitions and transition couplings. Generally in the present invention, the occurrence of a coupling between a first quantum transition and a second quantum transition can be measured for a number of said transitions simultaneously.

A preferred method of the present invention comprises the steps of: generating at least one pulsed light field; generating spatially separated light fields as diffracted orders of a diffractive optical component; arranging a modified telescope for defining at least three optical paths intersecting a common object point and a common image point, wherein at least two said optical paths are modified in separation from that possible to define with a single unmodified telescope; positioning said diffractive optical component at said object point so as to define a common overlap volume for light fields containing said image point; arranging for laser field waists at said overlap volume, wherein each waist size is more than 400 times the respective light field mean wavelength; generating a signal light field within said sample by the interaction of said light fields; transforming said signal field from said sample to a corresponding optical far-field signal variation; measuring said far-field signal variation, identifying the occurrence or the lack of occurrence of coherently coupled quantum transitions or energy transfer within said sample thereby.

A preferred apparatus embodiment of the present invention comprises: at least one source being operable to emit a pulsed light field for directing to a diffractive optical component; said diffractive optical component defining at least three optical paths from one optical path; a modified telescope defining at least three optical paths intersecting a common object point and a common image point, wherein at least two said optical paths are modified in separation from that possible to define with a single unmodified telescope; said diffractive optical component disposed at said object point so as to define a common overlap volume for light fields containing said image point at which sample for molecular analysis is in use disposed; at least one optical component arranged such as to define field waists at said overlap volume with each waist size more than 400 times the respective light field mean wavelength; a means for resolving an angular variation of light emission from said sample, said means comprising at least one optical component arranged for transforming a light field variation in a plane within said overlap volume to a corresponding optical far-field light variation in a plane at which a light detector is disposed.

In one embodiment, said light detector comprises a two-dimensional detector array, providing a means for resolving the angular variation of light emission from a molecular sample in two dimensions. This provides for the advantageous rapid measurement and distinguishing of numerous coherently coupled quantum transitions or numerous energy transfers.

In one embodiment, said modified telescope comprises three telescopes with a relative tilt between the telescope optical axes. In an alternative arrangement, said modified telescope comprises one telescope with three optical periscopes disposed in separate optical paths of said telescope, for modifying the transverse separation of three optical paths.

This preferred embodiment advantageously provides for a robust, flexible and straightforward apparatus. For example, it can provide a net reduction in the number of optical components over other embodiments of the present invention. It can be arranged for angularly dispersing the signal according to the signal energy, advantageously reducing the overlap of detected signal features and increasing the information that can be revealed from a single ARC map thereby. As shown herein, this embodiment advantageously distinguishes coherent quantum couplings and quantum energy transfers using a single light pulse. Further, this embodiment may be arranged such as to advantageously increase the efficiency of signal emission due to an increase in phase matching within the sample whilst also increasing the apparatus energy resolution. Further, arrangements of this embodiment either permit, or increase, an angular separation of the signal from that of other light fields, advantageously providing for an increase in the ratio of detected signal to background light.

An alternative method of the present invention comprises the steps of: generating at least three spatially separated pulsed light fields; directing said light fields along converging optical paths to a common overlap volume; arranging for laser field waists at said overlap volume, wherein each waist size is more than 400 times the respective light field mean wavelength; positioning sample within said overlap volume; generating a signal light field within said sample by the interaction of said light fields; transforming said signal field variation in two-dimensions from said sample to a corresponding optical far-field signal variation using a focusing optical component measuring said far-field signal variation in two-dimensions, identifying the occurrence or the lack of occurrence of coherently coupled quantum transitions or energy transfer within said sample thereby.

An alternative apparatus embodiment of the present invention comprises: one or more sources for generating at least three spatially separated pulsed light fields; a means for directing said light fields along converging optical paths defining a common overlap volume within which sample for molecular analysis is in use disposed, said means comprising at least one optical component arranged such as to define waists at said overlap volume with each waist size more than 400 times the respective light field mean wavelength; a means for resolving an angular variation of light emission from said sample in two-dimensions, said means comprising at least one focusing optical component arranged for transforming a two-dimensional light field variation within said overlap volume to a corresponding optical far-field light variation in a plane at which a two-dimensional light detector array is disposed. This embodiment preferably comprises a spectral filter or an angular dispersion optic, positioned such as to modify the signal light detected.

In preferred embodiments of this invention, said means for resolving an angular variation of light emission from said sample comprises one focusing optical component wherein the optical separation of said focusing optical component from said light detector is equal to the optical component focal length. This arrangement advantageously provides for an optimum angular resolution of the signal emission whilst providing for a compact and robust apparatus. This arrangement is optimised through selection of said optical component focal length for providing sufficient sampling of the signal point spread function by a defined number of detector pixels whilst containing the signal emissions to within a defined detection area. The detector may also be optionally combined with associated imaging optics.

In the aforementioned preferred embodiment, said telescope modification defines a component of angle modification, termed a resolving angle ($\alpha$) between said optical paths at said image point, and a resolving axis is defined in the plane containing said resolving angle. In all embodiments of the present invention, including the aforementioned alternative embodiment, the resolving angle may be described more generally as the angle between light frequency group fronts at the field overlap volume. For the above alternative embodiment, where comprising the crossing of typically generated light fields, the resolving angle is defined straight forwardly as the angle between tight field optical paths at the overlap volume and the resolving axis is defined in a plane containing said optical paths. In the present invention, a combination of two resolving angles in separate resolving axes provides for a two-dimensional mapping of far-field signal variation, from which a molecular analysis may be derived.

An increase in a resolving angle advantageously provides for a proportional increase in energy resolution from the apparatus, due to an increase in the displacement of signal emission at the detector plane. An increase in light field waist sizes at the sample also advantageously provides for a proportional increase in energy resolution from the apparatus, due to a corresponding decrease in the angular spread that supports a signal feature at the detection plane resulting from diffraction.

An increase in light field waist sizes further advantageously provides for an increase in the ratio of the detected signal intensity relative to that of background light. By way of example in the embodiments shown, due to diffraction an increase in waist size allows for a corresponding decrease in signal feature size at the detector. This permits an increase in signal intensity whilst linear scatter from the sample, which is non-directional, remains defocused at the detection plane. An increase of light field waist sizes at the sample is ultimately limited by the available light source intensity, the sample dimensions, the optical clearances in the apparatus, the optical aberrations imparted by the sample holder and other optics and, the preferred temporal resolution for the apparatus. Mappings for the far-field signal variation in two-dimensions are quantified in terms of resolving axes, resolving angles and the energies of light interaction with the molecular sample. A condition relating the apparatus energy resolution, the light field waist sizes and a resolving angle is described by the teachings herein, providing a limiting condition on the arrangement of optical components for all embodiments of the present invention. In a straight forward limiting condition for arrangements of the present invention, waists are defined at said overlap volume with each waist size more than 400 times the respective light field mean wavelength.

Embodiments preferably comprise a source being operable to emit a pulsed light field with an optical bandwidth more than one twentieth of the optical wavelength and a divergence less than 5 times the diffraction limit. Use of a light source with a broad bandwidth advantageously provides for the mapping of quantum electronic transitions with largely differing transition energies. An arrangement for a low divergence of light fields at the sample advantageously provides for a high angular resolution of signal field variation.

A preferred source of electromagnetic radiation for the present invention is a high pulse energy (~mJ), ultra-fast pulsed (sub-100 fs) laser that contains a broad and coherent laser bandwidth spanning the optical spectrum, with a near-diffraction limited spatial quality. A short pulse duration provides for a large light intensity, which results in efficient nonlinear signal generation in the sample. This also results in an advantageous coherence between wavelengths across the laser spectrum. For an ARC four wave-mixing analysis of a sample containing typical resonant optical transitions in the visible region of the optical spectrum, the preferred light field waist size is between 1 mm and 10 mm with a preferred light pulse energy is between 1 and 100 µJ/pulse at the sample.

The invention will now be described solely by way of example with reference to the accompanying figures in which:

FIG. 1 shows an illustration of ARC four-wave-mixing, with: (a) an arrangement of light field optical paths; (b) a time-ordered light-matter interaction sequence shown as an energy level diagram for which solid and dashed lines represent real and conjugate light-field interactions that combine in pairs to represent a photon exchange, and where $T_{12}$ and $T_{23}$ are times between light-field interactions; (c) a representation of light-vector summations and the resultant signal deviation resulting from a coherent coupling between quantum transitions (horizontal deviation) and an energy transfer between quantum transitions (vertical deviation); (d) an illustration of the resultant mapping of signal intensity deviation at the detector.

FIG. 2 shows: (a) an embodiment of an ARC wave-mixing apparatus comprising a means for directing said light fields along converging optical paths defining a common overlap volume within which sample for molecular analysis is in use disposed, and a means for resolving an angular variation of light emission from said sample in two-dimensions; (b) arrangements of a detector in the optical far-field. Labelled are resolving angles, $\alpha_h$ and $\alpha_v$ in each of two resolving axes in the horizontal and vertical planes for the arrangement as shown. Each resolving axis contains two optical paths within the overlap volume.

FIG. 3 shows: (a) an embodiment of an ARC wave-mixing apparatus comprising a diffractive optical component, and a modified telescope further comprising three optical telescopes with separate optical axes. The components of angle modification between each of two pairs of optical paths at said image point are termed resolving angles, $\alpha_h$, $\alpha_v$. Labelled is one of said resolving angles, $\alpha_h$ in a resolving axis defined in a plane containing two optical paths within the overlap volume (in the horizontal for the apparatus as shown); (b) a preferred arrangement for a telescope curved mirror set.

FIG. 4, shows: (a) an embodiment of an ARC wave-mixing apparatus in which an alternative modified telescope comprises three optical periscopes disposed in the optical paths between said common object point and said common image point; (b) a combined periscope component viewed in cross section such as to be transverse to the direction of light field propagation and; (c) said periscope component viewed in cross section such as to contain the direction of light field propagation.

FIG. 5 shows: (a) the positions of light field optical paths in the far-field of the sample for the embodiments of FIGS. 3 and 4, this for light fields of comparable mean wavelength arranged with components of angle modification, $\alpha_h$ and $\alpha_v$ such as to form of a square geometry in the far-field of the sample; (b) the signal mapping at the detector for the arrangement of figure (a); (c) by way of illustration of the principles involved, an alternative optical path arrangement for the apparatuses of FIGS. 3 and 4, in which light fields 2 and 3 are swapped in position, but the components of angle modification of said fields, $\alpha_h$ and $\alpha_v$ remain the same as that for figure (a) and the $k_1$ light field is generated as the zero order light field from the diffractive optic; (d) the signal mapping at the detector for the arrangement of figure (c). Mappings are as determined from calculation of the light field vector addition for the time-ordering as shown in FIG. 1(b).

FIG. 6 shows example light-matter interaction sequences for: a) a four-wave-mixing resonant infrared interaction, typified for light interactions with coupled vibration transitions; (b) a combination of resonant and non-resonant interaction such as typified in infrared-visible DOVE wave-mixing. These prior art pulse sequences are by way of example and will be apparent to those skilled in the art. Such light-matter interaction sequences are advantageously combined with the present invention.

FIG. 7 shows: (a) a time-ordered light-matter interaction sequence for an all non-resonant optical six-wave-mixing sequence of prior art which is advantageously combined with the present invention; (b) example positions of the light field optical paths and the detector, for six-wave-mixing with the embodiment of FIG. 2, showing the detector in positioned in the direction of light field 1; (c) example positions of the light field optical paths and the detector, for six-wave-mixing with the embodiment of FIG. 3 or FIG. 4, showing the detector advantageously separated from the other light fields directed to the sample; (d) an illustration of the resultant directions of signal deviation for the arrangements of both figure (b) and figure (c). For the arrangements of both (b) and (c), signal deviations derive from vibration couplings which provide for differences in the energies of non-resonant light field interactions. The mappings for both configurations are defined by the same resolving angles, $\alpha_h$ and $\alpha_v$. In both of figures (b) and (c), the detector is placed to detect the $+(\underline{k}_1-\underline{k}_{1'})+(\underline{k}_2-\underline{k}_{2'})+\underline{k}_3$ vector direction, which for the arrangement of figure (c) provides for an advantageous separation of the detected signal from other light fields.

FIG. 8 shows by way of example, all-resonant ARC transient grating images measured with the embodiment of FIG. 3 for a protein sample, LH2 in solution, with: (a) a map measured from said protein sample at a time delay of 1.3 ps. Two CCD images directly captured from optical filtering at (800+/−5)nm and (852+/−5)nm are summed, with intensity in arbitrary units; (b) full maps with no band-pass filtering at the detector, as directly captured, are overlaid with lines at $\beta=25.0°$; (c) maps with signal band-pass filtering at 880 nm (10 nm bandwidth), overlaid with a vertical and a 45° diagonal line and including an illustration of the feature displacements (dotted white arrows) associated with $\Delta$ (vertical) and $\delta$ (horizontal.

By way of illustrating some principles involved, FIG. 1(a) shows a simplified diagram for ARC four wave-mixing in which the emission is detected at the remaining vertex of the box formed by the three light fields 1, 2, 3 with angles $\alpha_h$ and $\alpha_v$ between light field optical paths in the horizontal and vertical planes respectively. The emitted signal is resolved with high angular resolution and in a compact arrangement by means not shown in this figure, and a two dimensional CCD detector 4 is used to measure the angular variation of the signal emission. The detector 4 is arranged in an optical path containing the sample with a wave-vector direction defined by $\underline{k}_s = -\underline{k}_1 + \underline{k}_2 + \underline{k}_3$ i.e., a sum of two light field wave-vectors differenced with a third light field wave-vector, said light field wave-vectors intersecting said overlap volume.

ARC wave-mixing may be applied in combination with prior art four and higher order wave-mixing schemes, with both the transient grating (TG) and echo pulse sequences and, resonant and non-resonant interactions. The wavelengths used may span the electromagnetic spectrum. By way of an explanation of the ARC method and apparatus embodiments, the resonant TG four-wave-mixing sequence is described in the main herein, in which pulses 1 and 2 are precisely overlapped in time and pulse 3 arrives with a controllable delay. FIG. 1(b) shows a light-matter interaction for this sequence that involves an energy transfer with a quantum defect, $\Delta = \omega_1 - \omega_3 = \omega_2 - \omega_S$ and a coupled coherence between two quantum transitions with a difference in energy, $\delta = \omega_1 - \omega_2 = \omega_3 - \omega_S$. The quantum levels depicted are typical for describing a molecular-electronic system, but equally FIG. 6(a) shows an equivalent sequence for interaction with molecular vibration quantum transitions using light source wavelengths in the infrared.

A source of electromagnetic radiation that is well suited for the present invention for application in the visible or near-infrared, is a titanium sapphire ultra-fast laser system at 1 kHz repetition rate with argon gas filled hollow fibre pulse compression (M. Nisoli, S. D. Silvestri, and O. Svelto, Appl. Phys. Lett. 60, 2793, 1996; J. S. Robinson et. al., Appl. Phys. B 85, 2006). This emits greater than 1 mJ in pulse energy, a 20 fs pulse duration, a spectrum that can span greater than 500 nm and a near-diffraction limited, stable light field. Spatial stability, angular stability and a near to diffraction limited output are advantageous for the measurement of light field angular variations in the present invention, as is required to provide for energy resolution from the apparatus. An increase in optical bandwidth advantageously allows for the mapping of quantum electronic transitions with largely differing transition energies. Shown by example herein, is the use of this source being operable to emit a pulsed light field with an optical bandwidth more than one twentieth of the optical wavelength and a divergence less than 5 times the diffraction limit.

A reduction in pulse duration delivered to the ARC apparatus advantageously provides for sensitivity to chemical and energy transfer dynamics in the sample matter and further advantageously provides for: an efficient generation of signal emission; and a sensitivity to coupled quantum coherences in the sample matter due to the spectrum exhibiting a degree of spectral coherence. The pulse duration of each of the light fields directed to the sample is preferably between 0.1 fs and 100 ns and further preferably between 1 fs and 10 ps.

Alternative light sources may be used for the present invention, where exhibiting one or more of the above properties. An increase in phase coherence between interacting wavelengths is advantageous in providing for an increase in sensitivity to coherent couplings between sample quantum transitions. Light fields may be provided by one or more sources and each light field may be arranged such as to provide an independent range of photon energy. An broad optical bandwidth spanning the visible spectrum from the ultra-violet to the near-infrared is optimal for the resonant probing of electronic transitions in a sample and their coupling to vibration transitions. A broad optical bandwidth spanning more than 4000 cm$^{-1}$ in the near-infrared, for example centred at 800 nm, is optimal for the non-linear Raman probing of vibration transitions. A source may be combined with multiple wavelength conversion devices such as nonlinear crystals, gases or otherwise for an advantageous probing of: resonant electronic molecular transitions in the visible region of the optical spectrum; vibration transitions through direct resonant interaction in the infrared; bonding electronic transitions through direct resonant interaction in the ultra-violet; or combinations thereof. A light field may also be provided by a solid-state, liquid or gas laser, a waveguide electromagnetic source, a surface generated source, a free electron laser, or otherwise. A light field as referred to herein, may equivalently be described as an electromagnetic field.

By way of explanation of the method principle, for a transient grating four wave-mixing pulse sequence FIG. 1(c) shows that a vertical deviation in signal emission results from a difference in the interaction frequencies of fields 1 and 3 (finite $\Delta$) corresponding to an energy transfer. This is uncoupled from a horizontal deviation in signal emission that results from a difference in the interaction frequencies of field 1 and 2 (finite $\delta$), corresponding to a coherent excitation of two coupled single electron transitions (a quantum electronic beating). The ability to deliver both the magnitudes and signs of $\Delta$ and $\delta$ derives from spatially extended interferences in the sample given by $-k_1+k_2$ and ensembles of identically emitting molecules are distinguished according to these interferences.

The angle of signal deviation is derived from FIG. 1(c) in the approximation of small angles between light field optical paths for well phase matched signal emission. For energy transfer, $|k_1|=|k_2|$ and the magnitude of $-k_1+k_2$ in the vertical plane as illustrated in FIG. 1(c)(ii) is given by both $\omega_2 \alpha_v$ and $\omega_S(\alpha_v+\Phi_v)$ which when equated simplifies to $\Phi_v=\alpha_v\Delta/\omega_S$, consistent with previous work (T. J. Butenhoff, and E. A. Rohlfing, Journal of Chemical Physics 98, 5460, 1993). This can be visualised as the scattering of light field 3 from a stationary population grating (of ~10 μm period where sensing ~850 nm electronic transitions). For coherently coupled quantum transitions (quantum beats), $|k_1|\neq|k_2|$ and a projection of $-k_1+k_2$ in the horizontal plane as illustrated by the red line in FIG. 1(c)(iii), is given by both $\omega_S\Phi_h$ and $(\omega_1-\omega_2)\alpha_h$ which when equated simplifies to $\Phi_h=\alpha_h\delta/\omega_N$. This can be visualised as the scattering of light field 3 from propagating modulations in the sample polarisation (of a millimeter period for a coupling between electronic transitions differing by ~200 cm$^{-1}$ at 850 nm). These signal deviations are illustrated in FIG. 1(d). This and other illustrations of signal deviations (mappings) contained herein are also reproduced by three dimensional light field ray-vector numerical addition, as a function of the wavelengths of light field interactions.

FIG. 2(a) shows an embodiment of the present invention, comprising: one or more sources for generating at least three spatially separated pulsed light fields 1, 2, 3; a means for directing said light fields along converging optical paths defining a common overlap volume 17 within which sample for molecular analysis 11 is in use disposed, said means comprising at least one optical component 29 arranged such as to define waists at said overlap volume with each waist size more than 400 times the respective light field mean wavelength; a means for resolving an angular variation of light emission from said sample in two-dimensions, said means comprising at least one focusing optical component 13 arranged for transforming a two-dimensional light field variation within said overlap volume to a corresponding optical far-field light variation in a plane at which a two-dimensional light detector array 4 is disposed. Arrangements preferably comprise a source being operable to emit a pulsed light field 36 with an optical bandwidth more than one twentieth of the optical wavelength. A means for directing light fields to converge and overlap 29 may comprise multiple accurately aligned and positioned optical components, in one arrangement, a spectral filter or dispersive optical element 14 is arranged for conditioning the signal according to emission wavelength. The far-field signal variation is measured, identifying the occurrence or the lack of occurrence of coherently coupled quantum transitions or energy transfer within said sample thereby.

FIG. 2(b) illustrates arrangements of a detector in the optical far-field for the embodiments shown in FIGS. 2, 3 and 4, for four wave-mixing where the light fields are close in mean wavelength. Detectors may be positioned at the vertices 4, 5, 6 defining three different parallelograms More generally for four wave-mixing, and including for the case of light fields differing significantly in wavelength, these signal emission directions are defined by the vector sums $-k_1+k_2+k_3$, $k_1+k_2-k_3$ and, $k_1-k_2+k_3$ respectively. For light fields close in wavelength, a preferred vertex for the positioning of a detector completes a parallelogram closest in form to that of a rectangle ($-k_1+k_2+k_3$ as shown), this for an advantageous maximisation of signal intensity and an advantageous accuracy in interpretation of feature positions that results from an optimisation of phase matching (conservation of photon energy and momentum). The parallelogram is preferably a square or rectangle, for advantage in distinguishing two resolving axes as orthogonal dimensions.

As will be apparent to those skilled in the art, the optical far-field of an axis or plane in the overlap volume refers to an axis or plane transverse to an optical path for containing a light field variation that is a scaled equivalent of that produced for an arbitrarily large distance of light propagation from the overlap volume. The optical far-field as such contains a representation of the angular distribution of the signal emitted from the sample.

The present invention preferably comprises a focusing optical component 13 defining an optical path intersecting the overlap volume and the light detector, wherein the optical separation of said focusing optical component from said common overlap volume is equal to the optical component focal length.

The optical component focal length is defined for an axis parallel to a resolving axis at said overlap volume and transverse to said optical path. Where two resolving axes define two-dimensions, said focal length is defined the same in two dimensions and said focusing optical component may be provided by a spherical lens or otherwise.

An arrangement using a focusing optical component provides for an advantageous apparatus compactness, and advantageous apparatus stability thereby. In typical prior art four wave-mixing configurations, an example signal field waist size of 50 microns at a wavelength of 0.5 microns requires a free propagation distance of only a few centimeters in order to provide a far-field signal representation (note that due to the dominance of diffraction, this arrangement is not applicable in the present invention). In contrast in the present invention, a significantly larger signal field waist size in the sample is required for high instrument energy resolution. This in turn requires a disadvantageously large distance for free-propagation to an optical far field distribution. By way of example in the present invention, free propagation of a diffraction limited signal field with a waist size of 5 mm would require a propagation distance significantly greater than 200 m at wavelength 0.5 microns, in order to reproduce an optical far-field distribution.

An arrangement using a focusing optical component further advantageously provides for a scaling of the signal field angular variation to the detector area and pixel spacing. An optimum focal length for the focusing optical component 13 can be defined based on the teachings herein and combining with the equation for light diffraction (Lasers, A. E. Siegman). An increase in the optic focal length results in an increase in the minimum widths of signal features at the detector plane, and results in an increase in the deviation of the signal at the detector. As such, an optimum focal length advantageously provides for sampling of the desired signal feature widths whilst permitting the capture of a desired range of signal emissions within a detector area. The focal length is between 0.01 m and 10 m and is preferably between 0.2 m and 1 m for the example of light field wavelengths in the near-infrared; light field bandwidths of 100 nm; light field waist sizes on the order of millimeters at the sample; a CCD detector with 20 μm pixel size and; a 1 cm×1 cm detection area.

The present invention is further preferably arranged with the separation of said focusing optical component from said common overlap volume equal to the optical component focal length. This arrangement advantageously provides for reduced tolerances in the positioning of components for the accurate measurement of signal feature separations at the detector. Further, this arrangement provides for an undistorted signal phase profile at the detector, advantageously providing for reproducible measurements where embodiments are combined with heterodyned detection in which a further field interferes with the signal field at the detector.

Transformation of a light field variation at the sampling position to a corresponding optical far-field variation is alternatively provided by means of a compound optic comprising multiple optical elements such as lenses or curved mirrors (mounted together or separately) for an advantageous apparatus compactness. A compound optic can be described by first and second principal planes and a compound optic (effective) focal length for each of two transverse axes.

A focusing optical component converges collinear optical paths and comprises any one of: a lens of positive focal length; a concave mirror; a Fresnel zone plate: a graded index lens; or otherwise. For all embodiments of the present invention, the optical component 13 is preferably a lens or concave mirror for an advantageous high optical quality and minimisation of background scatter.

As will also be apparent to those skilled in the art, an optical separation between two components refers to the net optical path length for light field propagation between the two components, and an optical path may be folded or otherwise.

In the present invention, a resolving angle, α is equivalent to the angle between light pulse energy (frequency group) fronts at the sampling position. By way of an example, a pulse duration of 20 fs provides for a light disc with a thickness of 7 microns in the direction of travel, and a width of millimeters. A disc of such energy is typically aligned perpendicular to the direction of travel of light. For the case of $\alpha_h$ and $\alpha_v$=0 in FIGS. 3 and 4, these discs of light overlap at the sample, providing for maximum temporal resolution but not providing for an ARC spectral resolution (a vertical or horizontal signal deviation due to coupled quantum transitions). Where $\alpha_h$ and $\alpha_v \neq 0$, the discs of light do not fully overlap in time at the overlap volume, which provides for a reduced temporal resolution and a concomitant ARC spectral resolution in each of the vertical and horizontal planes. This relationship between a temporal and a spectral resolution is that of the uncertainty principle and this provides a further intuitive understanding of all arrangements in the present invention.

Preferred embodiments of this invention are shown in FIGS. 3 and 4. These embodiments may be arranged for advantageously separating the signal field from other light fields, and for advantageously increasing the phase matching for signal generation whilst maintaining spectral energy resolution. In terms of robustness and optical stability, optical components for the generation and manipulation of multiple optical paths 29 are replaced by a straight forward arrangement with a reduced number of optical components such as a single mirror and intensity attenuator in component 37. Sensitivities to variation in the optical path angle and to the spatial intensity profile of the input light field 23, are advantageously decreased due to a matching of optical fields from the diffractive optic and, due to a combined mounting of optical components 26, 27 (or 32, 33) that reduces relative misalignments that derive from component drift. The spectrum of each light field is optionally modified by the insertion of masks 30 in the spectral plane mid-way between the telescope (curved) optics, for an advantageous aid in the interpretation of ARC maps, or for a reduction of unnecessary light exposure at the sample for an advantageous reduction in sample toxicity.

FIG. 3 shows an embodiment of the present invention comprising: at least one source being operable to emit a pulsed light field 36 for directing to a diffractive optical component 25, said diffractive optical component defining at least three optical paths 1, 2, 3 from one optical path; a modified telescope 26 and 27 defining at least three optical intersecting a common object point and a common image point, wherein at least two said optical paths are modified in separation from that possible to define with a single unmodified telescope; said diffractive optical component disposed at said object point so as to define a common overlap volume 17 for light fields containing said image point at which sample for molecular analysis 11 is in use disposed; a means for resolving an angular variation of light emission from said sample, said means comprising at least one optical component 13 arranged for transforming a light field variation in a plane within said overlap volume to a corresponding optical far-field light variation in a plane at which a light detector 4 is disposed.

In the present invention arranged for four-wave-mixing, the diffractive optical component preferably provides four optical paths from horizontal and vertical +/−1 order diffraction. One of the light fields is preferably blocked within the telescope and the remaining three are relayed to the sample by three telescopes (comprising 6 curved optics) which are arranged with the diffractive optic positioned at an object point and the sample positioned at the corresponding image point. These points may also be referred to as telescope conjugate points (Optics, E. Hecht $3^{rd}$ ed.). A polariser 24 is disposed in the light field optical path to ensure polarisation purity. Turning mirrors 31 provide a folded optical path for an advantageous apparatus compactness and an overall reduction in optical aberrations imparted by the telescope.

FIG. 3(*b*) shows the telescope mirror set 26 of FIG. 3(*a*). In the arrangement shown, the mirrors comprising mirror set 27 are arranged with lateral separations that are greater than that in mirror set 26, for supporting an increase in the separations of the three fields 1, 2 and 3 on propagation between the telescope optics 26 and 27. In an alternative arrangement, mirrors of set 27 are arranged closer together than those of mirror set 26, for supporting a decrease in the separations of light field optical paths between the telescope optics.

FIG. 4 shows an embodiment in which said modified telescope comprises optics 32 and three periscopes 33 arranged symmetrically in the light field optical paths between the telescope optics. A periscope provides a means for modification of the transverse separation of a first optical path from a second optical path between said common object point and said common image point. A symmetrical arrangement of periscopes (see FIGS. 4(*b*) and 4(*c*)) advantageously provides for a reduction of telescope optical aberrations due to a minimisation of the telescope numerical aperture (NA).

Each periscope comprises at least two mirrors, or alternatively at least two total internal reflecting surfaces, or equivalent. Reflectors are spatially displaced, with one set of reflectors 35 preferably arranged surrounding the other set 34. In the arrangement shown, optical paths along which light fields are directed 1, 2, 3, are deviated by reflectors 34 and returned to the original propagation direction by reflectors 35, shown here to increase in the separation of optical paths. In an alternative arrangement, the optical paths are deviated first by reflectors 35, to provide a decrease in the separation of light field optical paths. In a further alternative embodiment, the optical paths are deviated first by reflectors 34 and are redirected by reflectors 35 to oppose the original propagation direction, to provide a folded apparatus with the advantage of compactness.

A continuous means of adjustment in the transverse separation of optical paths is provided by the translation of the separation of reflectors 34 relative to 35, said translation as illustrated in FIG. 4(*c*) in the direction of the optical paths. In one example, the preferred modification in the transverse separation of any two light field optical paths between the telescope optics is between 0 and +/−80 mm for telescope optics of 400 mm focal length, for advantageously minimising optical aberrations imparted by the telescope optics.

A telescope modification defines a component of angle modification, or equivalently resolving angle α, between optical paths at the sample. The associated resolving axis need not be defined in a plane containing optical paths generated by the diffractive optic, as illustrated by way of example in FIG. 5.

FIGS. 3 and 4 show the telescope conjugate points (object and image points) selected symmetrically about the telescope focusing optics 26 (or 32). In alternative arrangements, the diffractive optic and sample are arranged in an asymmetric arrangement about the telescope optics, positioned at alternative object and image points. Such an asymmetric arrangement introduces an angle between the light field optical paths within the telescopes. It remains however, that the present invention requires at least three optical paths intersecting a common object point and a common image point, wherein at least two said optical paths are modified in separation from that possible to define with a single unmodified telescope. Also, FIGS. 3 and 4 show arrangements wherein the telescope is of unit magnification. Other telescope magnifications may be arranged in alternative embodiments of the present invention.

The embodiments of FIGS. 3 and 4 show telescopes consisting of two concave optics in each telescope optical path. Alternative embodiments of the present invention comprise telescopes containing three or more focusing or diverging optics. A telescope optic comprises one of a mirror, a concave or convex reflecting surface, or a lens, for altering the divergence properties of one or more light fields. A means for adjusting said telescope modification comprises any one of: a reflective optic with means for adjustment of angular alignment; a refractive optic with means for translation transverse to a light field optical path; an optical wedge.

A device 30 for light field spectral modification is disposed in one or more light field optical paths 1, 2, 3 and preferably as shown in the optical far-field of the diffractive optic with separation from a telescope optic of one telescope optic focal length. This positioning provides for advantageous spectral resolution, combined with flexibility and reduced apparatus complexity. The device 30 may comprise any one of: a material edge, as shown; an optically absorbing material; an optical mirror; a partially transmitting optical material; a spectral intensity filter; a spectral phase filter; a material with a transverse variation in optical thickness. In one embodiment, a spatial variation in optical transmission is provided by one or more transmitting optical filters. In an alternative embodiment, a light field modification is provided by means of active acousto-optic tuneable filters, positioned as shown or otherwise.

For an advantageous increase in the stability and resolution of detected signal features, an optical aperture is disposed in an optical path between a light source 36 and the diffractive optic 25. At least one of a lens or concave mirror is positioned such that said aperture in an optical far-field plane of said diffractive optical component. The aperture may constitute: an optical mask: the exit of an optical fibre or waveguide used for the generation of wavelength components; a waveguide; the boundary of a medium; an adjustable aperture; an edge-graduated aperture. In one embodiment, a hollow fibre for the generation of light comprises said aperture.

A relationship for the apparatus energy resolution, $E_{res}$ in each of the horizontal and vertical planes for the embodiments as shown in FIGS. 2, 3 and 4 is given below. This is given by equating the angle of feature deviation $\Phi_{v,h}$ (as derived above) with a minimum permissible resolution diameter (apparatus point spread function) at the detector. This point spread function is given by the diffraction equation and is defined by the arrangement of optic 13, accounting for the waist size, wavelength and beam quality parameter of the emitted signal ($M^2$). $E_{res}$ is derived to be inversely proportional to the product of a light field waist size at the common overlap volume 17, W (in microns) and the corresponding resolving angle, $\alpha_{h,v}$ (in radians), as follows:

$$\text{Instrument energy resolution: } E_{res}(h,v) = 8000 \text{ cm}^{-1} M^2 / W_{h,v} \alpha_{h,v}$$

The light field waist is defined in a resolving axis, this in a plane that contains a resolving angle at the sample. The beam parameter, $M^2$ accounts for the light field optical quality and aberrations due to the sample or otherwise, where $M^2=1$ for diffraction limited light (Lasers, A. E. Siegman, 1986). A waist size is defined as the full width half maximum (FWHM) of intensity in an axis transverse to the respective light field optical path. The waist size may alternatively be given in terms of the electric field $e^{-1}$ half width where W(amplitude, $e^{-1}$)=W/1.2 as will be apparent to those skilled in the art. An energy resolution may be advantageously further increased by taking a weighted determination of the centres and widths in the post-processing of spatially discrete features.

By way of example, an apparatus energy resolution (in Δ or δ) of $E_{res} \leq 1000$ cm$^{-1}$ provides for a degree of useful application with the present invention, this corresponding to a resolution of ≤100 nm at a signal wavelength of 1 μm, or ≤4 nm at a signal wavelength of 200 nm. This instrument resolution is provided by W≥8/α, for diffraction limited light fields in the absence of significant aberrations. As such, each waist size magnitude is more than eight times the reciprocal magnitude of the angle between said light field optical paths at said overlap volume, said waists defined in microns in the plane containing said angle, said angle defined in radians. By way of another example, a more generally useful instrument resolution of $\leq 20$ cm$^{-1}$ (in $\Delta$ or $\delta$) is provided by W$\geq$400/$\alpha$.

Under a more straight forward constraint for the present invention, an apparatus is arranged such as to define waists at said overlap volume 17 with each waist size more than 400 times the respective light field 1, 2, 3 mean wavelength. Satisfying this condition permits signal light emission to be angularly resolved in a typical embodiment of the present invention. For example, for a light field with a mean wavelength of 1 µm, this condition leads to W$\geq$400 µm. For the above selected energy resolution of $E_{res}\leq 1000$ cm$^{-1}$, this requires $\alpha \geq 20$ mrad=1.1°. A significantly larger waist size is required for a resolution of $\leq 20$ cm$^{-1}$ where keeping beam angles small in order to maximise signal phase matching through a sample volume, and a required beam waist size may be calculated using the above relationship for instrument resolution.

In keeping with the above relationship, an increase in a resolving angle advantageously increases the energy resolution for the apparatus. In the embodiment of FIG. 2, an increase in a resolving angle disadvantageously decreases the efficiency of signal emission due to a reduction in signal phase matching in the sample. In contrast, the embodiments of FIGS. 3 and 4 may be arranged for advantageously increasing both a resolving angle and signal phase matching.

Beam blocks and apertures 12 are arranged so as to intercept the light field optical paths 1, 2, 3 following transmission through the sample. Optical delay wedges 7, are arranged to condition relative pulse delays at the sample, comprising any of: beam splitters; translation stages; optical delay wedges; optical flats.

Light fields are directed to one side of the sample and the emitted signal is detected in transmission through the sample. In alternative embodiments, light fields are directed to the sample: from opposite sides of the sample; from the same side as that of signal detection; in total internal reflection from an interface which is in contact with the sample.

The light detector 4 preferably comprises a two-dimensional detector array such as a CCD, CMOS or silicon detector array, for an advantageous reduction in the accumulation time of a two-dimensional distribution of light intensity. In alternative embodiments, the detector is provided by a photochemical image recording medium such as a photographic film, a holographic storage medium or holographic film, a photorefractive medium, a scintillation recording medium or otherwise.

The present invention can produce a two-dimensional map by the capture of a single image. Alternatively, an apparatus comprises an optical component 9 disposed in an optical path intersecting said overlap volume for temporally modulating any one of light intensity, light spectrum, and light delay, providing a means for difference imaging thereby. This component is preferably connected to a computer 16 for providing the capture of two or more images with and without the detection of the signal emission. Image differencing advantageously reduces the relative contribution from undesired background such as that derived from sample emission or otherwise, or advantageously enhances a first signal feature relative to a second signal feature. In one embodiment, one of the light fields directed to the sample is optically delayed in time by means of a highly transmitting optical flat translated into and out of the light field, wherein the flat is silica or quartz for use with wavelengths between the ultra-violet and near-infrared. In one alternative embodiment, the spectrum of one of the light fields directed to the sample is alternately modified by means of a passive, electronic or acoustic spectral filter.

Sample matter 11 is disposed within the common overlap volume 17 defined for converging light fields, said sample matter comprising any one of a: gas; liquid; solid. Said sample matter can be in the form of a volume or surface layer. A sample container for a liquid molecular mixture is preferably one of: a container such as a tube or cell with light transmitting windows; a multiple sample array container; a fluid flow cell; a fluidic device. The sample container may be arranged such as to be translated or rotated. The entrance and exit facets of the sample container and also the interfaces that contain the sample are preferably mutually parallel, for an advantageous reproducibility of the angle of signal emission between sample changes and, to provide for spatial stability of detected signal features during sample translation or rotation.

The use of this invention with electromagnetic wavelengths between 0.1 nm and 1 mm will be apparent to those skilled in the art and based on the teachings herein. The light fields directed to the common overlap volume may resonantly or non-resonantly excite the sample via any of the following: electronic bond transitions; electronic molecular transitions; molecular vibration transitions; mixed electronic and vibration transitions. In one embodiment, light fields are arranged with wavelengths preferably between or spanning 230 nm and 1500 nm such as to excite delocalised molecular-electronic transitions in the sample molecules. In an alternative embodiment, the light field wavelengths are preferably arranged between or spanning 160 nm and 230 nm such as to excite molecular-electronic bond transitions such as the amide bond transition. In another embodiment for the excitation of molecular vibrations, the wavelengths are preferably arranged between or spanning 1.5 µm and 30 µm.

The light fields are preferably pulsed. A light pulse repetition rate is preferably selected in the range from single shot (single pulse) to 100 MHz by means of electronic control of an optical gate or otherwise, and is further preferably selected in the range of single shot to 10 kHz, for an advantageous high pulse energy whilst providing for rapid sampling throughput. An increase in the light pulse repetition rate whilst maintaining the light pulse energy results in an advantageous increase in signal power and a competing disadvantageous increase in the sample thermal load and sample toxicity.

An optical component for the control of a pulse delay comprises any of: an optical delay wedge pair 7 with translation control; an optical flat 28 and; a mirror with translation control. Optical wedges typically provide a relative pulse delay of between 0.1 fs and 10 ps with advantageous fine control. Preferred optical materials for optical flats and wedges are silica and quartz for use with light wavelengths of less than 3000 nm and, calcium fluoride for use with light wavelengths greater than 3000 nm. A relative light pulse delay of up to 50 ns may be provided by the translation of mirrors mounted on translation stages. A longer light pulse delay may be provided by the selection of separate light pulsed emissions from a source.

In one embodiment, an arrangement for heterodyned detection comprises a further optical path between a source 36 and the light detector 4 for directing a light field to overlap at the detector and to interfere with the signal light field.

Modification of the polarisation of the light fields directed to the sample and of the polarisation detected, is provided for by means of one or more wave-plates 8 and a detector polariser 15, for an advantageous increase in sensitivity to the occurrence of coupled quantum transitions or energy transfer within said sample, or for an advantageous decrease in the detection of background non-resonant nonlinear emission.

For advantageously selecting or differentiating a desired signal field over other fields, one embodiment comprises an optical spectral filter 14 disposed in an optical path intersecting the overlap volume 17 and the light detector 4 for modification of the spectrum of light detected. For modification of the spatial distribution of the signal light detected, an alternative embodiment comprises: a spectral angular dispersive optical component disposed in the optical path intersecting said overlap volume and said light detector, said angular dispersive optical component further comprising any of a diffraction grating; a optical prism; an acousto-optic crystal. In the preferred embodiments as shown in FIGS. 3 to 5, the spatial distribution of the signal light detected is dispersed according to the signal wavelength without a requirement for said angularly dispersive component 14, with advantages that include a reduction in apparatus complexity and an increase in apparatus robustness.

By way of explanation for the embodiments as shown in FIG. 3 or FIG. 4, FIG. 5(a) includes a representation of the angular dispersion of each light field along the respective diagonals of a box geometry. Angle deviations in both the horizontal and vertical planes are given by the diffraction equation, $\theta_{diff} = \lambda_S/d_S$ for a wavelength, $\lambda_S$ and a grating ruling separation, $d_g$. As a result, the dimensions of the box geometry increase with wavelength, such as to extend the signal emission along a diagonal according to $\theta_d = \sqrt{2}\lambda_S/d_g = 2\sqrt{2}\pi c/\omega_S d_g$. The degree of signal dispersion is derived and is also numerically calculated by three-dimensional wave-vector addition for this and other arrangements in the present invention.

FIG. 5(b) illustrates how the position of the detected signal maps to $\lambda_S$, $\Delta$, and $\delta$. The use of parallel aligned telescopes ($\alpha_h = \alpha_v = 0$) gives sensitivity to $\omega_s$ only. The present invention requires a relative tilt of $\alpha_h$ and $\alpha_v$ between the light field optical paths within the telescopes, whilst maintaining common object and image points. For the embodiment of FIG. 2, a resolving angle is the total angle between two light field optical paths at the sample, in each the horizontal and vertical planes ($\alpha_h$ and $\alpha_v$). For the preferred embodiments shown in FIGS. 3 and 4 however, the resolving angle is provided by the angle of modification between optical paths at the image point, derived from modification of the transverse separations between optical paths from that possible to support with a single telescope arrangement. As such, a resolving axis may be arranged in any direction relative to the planes of light field separations.

FIGS. 3 and 4 are shown with resolving angles arranged in the same plane as an angle between light field optical paths from the diffractive optic 25 ($\theta_{diff}$). For this, the resolving angles may be arranged with a positive sign, increasing the total angle between light field optical paths at the sample for an advantageous increase in light field clearance from optical component mounts within the apparatus, as shown in FIG. 5(a). Alternatively the resolving angles may be arranged with a negative sign, decreasing the total angle between light field optical paths at the sample for an advantageous increase in the efficiency of signal emission resulting from an increase in phase matching (S. Mukamel, *Principles of nonlinear optical spectroscopy*, Oxford University Press, 1995).

By way of illustration of the principles involved, FIGS. 5(c) and 5(d) show an alternative configuration and associated mapping determined from calculation of the light field vector additions for the time ordering of FIG. 1(b). Fields 2 and 3 are swapped in position, but and the components of angle modification of said fields, $\alpha_h$ and $\alpha_v$ remain the same as that for FIGS. 5(a) (and 1(a)). As such the optical paths are instead arranged in a plane perpendicular to the angle between fields provided by the diffractive optic ($\theta_{diff}$). By way of further example, the $k_1$ light field is generated as the zero order light field from the diffractive optic. For this configuration, the signal mapping at the detector shows no signal wavelength dispersion. The mapping in FIG. 5(d) is the same as that for FIG. 1(d) (the embodiment of FIG. 2) and, the vertical and horizontal displacements are the same as that shown in FIG. 5(b), illustrating that a mapping is defined by the directions and magnitudes of the components of angle modification (which are common to these example arrangements).

In further embodiments of FIGS. 3 and 4, a resolving angle may be arranged in any other specified axis. For example, a single resolving axis (containing a single angle of modification) arranged at 45° provides for a two-dimensional mapping of light field excitation energy vs. signal emission energy, with a transient grating pulse sequence. In this arrangement, the single resolving axis is orthogonal to the axis for spectral signal dispersion. Where an arrangement comprises two resolving angles, they are preferably arranged to be mutually perpendicular for an advantageous separation of quantum coupling mechanisms in ARC maps.

The diffractive optical component 25 preferably comprises two spatially periodic diffractive rulings that are mutually perpendicular, arranged on a single optical element or otherwise. A transmission diffractive preferably comprises a surface profile in silica, quartz, or another material that substantially transmits the input light whilst remaining robust to high peak electromagnetic power. The diffractive optic may be etched, ruled or otherwise. An alternative embodiment comprises one or more reflective diffractive optical elements that are metal coated, dielectric coated or otherwise.

The line density of a diffractive optic is optimally selected dependant on the light wavelengths to be used, so as to provide $\overline{\theta}_{diff}$ in the horizontal and vertical planes of between 0.1° and 100°, and preferably between 2° and 10° so as to balance the contradictory requirements of decreasing optical aberrations imparted to the light fields whilst allowing for light field clearances from optical mounts within the telescope apparatus. In the embodiments shown, the diffractive optic line density is preferably between 15 and 150 rulings/mm for use with a light wavelength of 500 nm. In one embodiment, a diffractive optic with a spatially varying line density is translated to provide modification of $\overline{\theta}_{diff}$, providing a means for apparatus optimisation over a large range of wavelengths thereby.

The interaction pathway illustrated in FIG. 6(a) is provided by three infrared light fields 1, 2 interacting resonantly with vibration transitions. The signal intensities of features in the present invention are dependent on the couplings between said vibrations. The interaction pathway illustrated in FIG. 6(b) is provided by infrared light fields 1, 2 interacting resonantly with vibration transitions in the sample, in addition to a near-infrared (or otherwise) light field 3 interacting non-resonantly with the sample, in a mechanism referred to as Doubly Vibrationally Enhanced (DOVE) four wave-mixing in prior art. An array detector is placed so as to detect the vector phase matched signal output, for the example pathways as shown in FIG. 6, in the vector summed direction of $-k_1 + k_2 + k_3$. Therefore as for other four-wave-mixing embodiments of the present invention, ARC-DOVE embodiments comprise a detector 4 arranged in an optical path containing the sampling position 11 with a wave-vector direction defined by a sum of two light field wave-vectors differenced with a third light field wave-vector, for each said wave-vector intersecting the overlap volume 17. Where the wave-vector of field 3 is significantly greater than that of fields 1 and 2, the detector is positioned close to field 3 in the optical far-field of the overlap volume 17 and field 3 is preferably blocked, or reduced in intensity by spectral filtering. For an ARC wave-mixing analysis of a sample via resonant infrared transitions (FIG. 6(a)), the preferred infrared light field waist sizes at the sample are between 1 mm and 10 mm with an energy of between 0.1 mJ and 100 mJ/field at the sample.

Six wave-mixing embodiments such as those shown in FIG. 7, comprise the overlap volume 17 and the light detector 4 arranged for intersection with an optical path with a wave-vector direction defined by a sum of three light field wave-vectors differenced with a sum of two light field wave-vectors, for each said wave-vector intersecting said overlap volume. As illustrated in FIG. 7(a), light fields for this example interact non-resonantly with the sample. For an ARC wave-mixing analysis of a sample via non-resonant interactions in the near-infrared region of the optical spectrum, the preferred light field waist size is between 1 mm and 10 mm with an energy of between 10 µJ and 10 mJ/pulse at the sample.

An apparatus configuration for the optical path arrangement shown in FIG. 7(b), is shown in FIG. 2(a), comprising a spectral selective element 30 and an optical spectral notch filter 14 for reducing the intensity of the third light field whilst permitting transmission of the signal at the detector. As illustrated in FIG. 7(b), the array detector 4 is positioned so as to detect the vector phase matched signal in the vector summed direction of $\Delta k_1 + \Delta k_2 + \Delta k_3$, where $\Delta k_i$ represents a difference of a pair of light-matter interactions with the i'th light field.

In an alternative preferred six-wave-mixing embodiment, the apparatuses of FIG. 3 or FIG. 4 are arranged so as to direct five light fields to the sample and the signal is detected in the direction $+(k_1-k_{1'})+(k_2-k_{2'})+k_3$ as illustrated in the detection plane in FIG. 7(c). The arrangement as shown in FIG. 7(c), uses a diffractive optic that generates all first order diffraction fields and a zero order diffraction field. This arrangement provides for a separation of the detected signal from that of any light field directed to the sample, advantageously providing for an increase in the ratio of detected signal to background light. As such, a spectral notch filter 14 is not required for this arrangement, further advantageously providing for an increase in the energy range over which couplings between quantum vibration transitions can be measured. Further advantageously, the apparatus configurations of FIGS. 3 and 4 provide for a straight forward means by which one light field 23 can provide all the required wavelength components in the present invention.

FIG. 7(d) illustrates the signal mapping at the detector, as determined from the calculation of light field vector addition. The same mapping results from both of the example arrangement of FIGS. 7(b) and 7(c) due to both of these arrangements having the same resolving angles $\alpha_h$ and $\alpha_v$ and associated axes (c.f. FIG. 5).

ARC six wave-mixing is advantaged over prior art six wave-mixing methods in providing for an increase in the ratio of detected signal to background light, derived from the use of a large waist size in combination with an optimum resolution of the angular variation in signal emission. This permits signal detection from samples of a reduced concentration over prior art. Further, due to large waist sizes which interact with a large area of sample, sufficient signal strength may be obtained from a thinner sample, permitting the reduction of sample thickness over that of prior art. Any one of these properties provides for an advantageous increase in the ratio of the detected signal to cascaded or sequential third order light emissions as will be apparent to those skilled in the art.

Other wave-mixing schemes of prior art of otherwise, may be combined with the present invention as will be apparent to those skilled in the art based on the teachings herein. For example, other wave-mixing schemes include a component of sum-frequency generation or, mixed resonant-nonresonant light-matter interaction.

By way of an example demonstration of the present invention, FIG. 8 shows measurements from the present invention employing all-resonant ARC-TG four wave-mixing (transient grating pulse sequence). For this, the embodiment as shown in FIG. 3 was arranged with $\alpha_h=2.1°$ and $\alpha_v=1.8°$. The sample was contained between optical transmitting silica windows. The windows were optically flat of thickness 1 mm and 2 mm. The sample (a protein, LH2 in solution which has strong electronic dipole transitions near to 800 nm and 850 nm) was of thickness 100 µm, which in combination with the small angles between light field optical paths in this experiment ensured that phase matching effects do not contribute significantly to our experiment. The signal intensity was calculated to be within 0.1% of the maximum possible for all measurements. All figures shown were for an excitation probability of 0.1 per molecular pigment in the sample illuminated volume, given by a light pulse energy of 1.1 µJ/field at the sample within a light intensity waist of 4.1 mm.

FIG. 8(a) shows the overlay of two consecutive ARC-TG maps using optical band-pass filtering (10 nm bandwidths) 14 at 800 nm and 852 nm. A delay time of 1.3 ps allowed for the relaxation of electronic coherences ($\delta \sim 0$). The 852 nm filtered emission is detected to be shifted diagonally from that of the 800 nm filtered emission, as expected from FIG. 5(b). The measured vertical displacements of +2.05 and −1.90 mrad between features corresponds to $\Delta = \pm 770$ cm$^{-1}$ for downhill ($\Phi_v$ and $\Delta$ positive) and uphill ($\Phi_v$ and $\Delta$ negative) transfer respectively. This is consistent with energy transfer being derived from the peak excitations determined separately for the pigments.

FIG. 8(b) demonstrates the ability to capture an ARC wave-mixing map using a single light pulse. Measured ARC-TG maps are shown for two time delays without spectral filtering. As such, the signal emission is measured simultaneously at all photon energies with a single CCD captured frame. A peak detector count from this figure of $1 \times 10^6$ with a standard laboratory CCD (accounting for neutral density filters 14) demonstrates that a single ultra-fast light pulse is sufficient to deliver a full two-dimensional ARC image.

A measured 0.8 ps lifetime for energy transfer from one pigment to the other agrees with standard TG measurement. The features are observed to be aligned to an angle of $\beta = 25.0°$ from the vertical at long time delay (as overlaid) which agrees with that calculated from the equations given above, according to a range of emission energies being derived from a single excitation energy (homogenised energy reorganisation, $d\omega_\alpha/d\omega_S = 0$).

FIG. 8(c) demonstrates sensitivity of the ARC-TG to a coherent coupling between quantum transitions, this example being for electronic quantum transitions. This figure was detected using 10 nm bandwidth filtered detection at $\lambda_S = 880$ nm (11,360 cm$^{-1}$). As in FIG. 8(b), reflection symmetry was seen about the diagonal at zero time delay, with the upper feature resulting from the TG interaction time ordering (as labelled). The feature marked as B850-B850 (internal protein pigment energy transfer) was displaced vertically upwards by 0.73 mrad and horizontally to the left by 0.38 mrad, corresponding to $\Delta = +260$ cm$^{-1}$ and $\delta = +120$ cm$^{-1}$ (see FIGS. 1(b)

and 5(b)). The finite value of δ observed, corresponds to a coherent coupling between electronic quantum transitions (quantum electronic beating).

An ARC mapping can permit a direct quantification of the interaction energies of each light field with the sample, this simultaneously for an arbitrary bandwidth. This is deduced from a measurement of δ, Δ and $\omega_S$ (see FIGS. 1(b), 5(b)). As an example, deduced for the feature in FIG. 8(c) marked as B850-B850 at zero delay time is $\omega_1=11,740$ cm$^{-1}$, $\omega_2=11,620$ cm$^{-1}$, $\omega_3=11.480$ cm$^{-1}$ and $\omega_S=11,360$ cm$^{-1}$. Given that the third interaction necessarily precedes the final scattering, the observed direction for this feature displacement requires a downward time ordering of the third and scattered light-matter interaction energies. Further characteristics of the map, such as the timescales of the molecular relaxations are consistent with that expected from separate photon echo and anisotropy measurements.

The foregoing description of the invention has been presented for the purpose of illustration and description and is not intended to be exhaustive or to limit the invention to the precise form disclosed. Many modifications and variations are possible in light of the above teaching. The embodiments were chosen and described to best explain the principles of the invention and its practical application, to thereby enable others skilled in the art to best use the invention in various embodiments and with various modifications suited to the particular use contemplated. The scope of the invention is to be defined in the following claims.

The invention claimed is:

1. An apparatus for molecular analysis in coherent optical wave-mixing, comprising:
   at least one light source of optical bandwidth more than one twentieth of the optical wavelength and divergence less than 5 times the diffraction limit;
   a generating means for generating at least three spatially separated pulsed light fields from said at least one light source;
   a converging means for directing said light fields along converging optical paths defining a common overlap volume of waist size more than 400 times the respective light field mean wavelength within which sample for molecular analysis is in use disposed;
   a resolving means for resolving an angular variation of light emission from said sample in two-dimensions, said resolving means comprising at least one focusing optical component and a two-dimensional light detector array, wherein the optical separation of said focusing component from said light detector is equal to the component focal length.

2. An apparatus according to claim 1, in which said generating means comprises a diffractive optical component, and in which said converging means comprises:
   a modified telescope comprising at least two curved mirrors or lenses, defining at least three optical paths intersecting a common object point and a common image point, wherein at least two said optical paths are modified in separation from that possible to define with a single unmodified telescope;
   said diffractive optical component disposed at said object point so as to define a common overlap volume for light fields containing said image point at which sample for molecular analysis is in use disposed.

3. An apparatus according to claim 2, in which said modified telescope comprises at least two optical telescopes with separate optical axes, said optical axes arranged to intersect said common object point and said common image point.

4. An apparatus according to claim 2, in which said modified telescope comprises at least one periscope disposed in a first optical path such as to modify the transverse separation of a first optical path from a second optical path between said common object point and said common image point.

5. An apparatus according to claim 2, comprising a component for modifying a light field electromagnetic spectrum disposed in at least one optical path between said object and image points, wherein said component further comprises any one of: a material edge; a spectral interference filter; a material with a transverse variation in optical thickness.

6. An apparatus according to claim 2, comprising: an optical aperture disposed in an optical path between said source and said diffractive optic; at least one of a lens or concave mirror arranged in an optical path between said aperture and said diffractive optical component such that said aperture is at an optical far-field plane of said diffractive optical component.

7. An apparatus according to claim 6, wherein a gas-filled hollow fibre or waveguide for light generation comprises said aperture.

8. An apparatus according to claim 1 or claim 2, wherein the optical separation of said focusing optical component from said common overlap volume is equal to the optical component focal length.

9. An apparatus according to claim 1 or claim 2, wherein said source comprises a gas filled hollow fibre.

10. An apparatus according to claim 1 or claim 2, wherein said source comprises a wavelength conversion nonlinear crystal.

11. An apparatus according to claim 1 or claim 2, comprising an optical spectral filter disposed in an optical path intersecting said overlap volume and said light detector for modification of the spectrum of light detected.

12. An apparatus according to claim 1 or claim 2, comprising a spectral angular dispersive optical component disposed in the optical path intersecting said overlap volume and said light detector for modification of the spatial distribution of detected light, said angular dispersive optical component comprising any of: a diffraction grating; a optical prism; an acousto-optic crystal.

13. An apparatus according to claim 1 or claim 2, comprising said overlap volume and said light detector arranged for intersection with an optical path of wave-vector direction defined by a sum of two light field wave-vectors differenced with a third light field wave-vector, for each said wave-vector intersecting said overlap volume.

14. An apparatus according to claim 1 or claim 2, comprising said overlap volume and said light detector arranged for intersection with an optical path of wave-vector direction defined by a sum of three light field wave-vectors differenced with a sum of two light field wave-vectors, for each said wave-vector intersecting said overlap volume.

15. An apparatus according to claim 1 or claim 2, comprising an optical component disposed in an optical path intersecting said overlap volume for temporally modulating any one of light intensity, light spectrum, and light delay, providing a means for difference imaging thereby.

16. A method for molecular analysis in coherent optical wave-mixing, comprising the steps of:
   generating at least three spatially separated pulsed light fields of optical bandwidth more than one twentieth of the optical wavelength and divergence less than 5 times the diffraction limit;
   directing said light fields along converging optical paths to a common overlap volume;

arranging for laser field waists at said overlap volume, wherein each waist size is more than 400 times the respective light field mean wavelength;

positioning sample within said overlap volume;

generating a signal light field within said sample by the interaction of said light fields;

resolving the angular variation of said signal light emission from said sample in two-dimensions with at least one focusing optical component and a two-dimensional light detector array by arranging the optical separation of said focusing component from said light detector to be equal to said focusing component focal length;

measuring said angular variation of signal light in two-dimensions, identifying the occurrence or the lack of occurrence of coherently coupled quantum transitions or energy transfer within said sample thereby.

17. A method for molecular analysis in coherent optical wave-mixing, said method comprising the steps of:

generating at least one pulsed light field of optical bandwidth more than one twentieth of the optical wavelength and divergence less than 5 times the diffraction limit;

generating spatially separated light fields as diffracted orders of a diffractive optical component;

arranging a modified telescope comprising at least two curved mirrors or lenses, for defining at least three optical paths intersecting a common object point and a common image point, wherein at least two said optical paths are modified in separation from that possible to define with a single unmodified telescope;

positioning said diffractive optical component at said object point so as to define a common overlap volume for light fields containing said image point;

arranging for laser field waists at said overlap volume, wherein each waist size is more than 400 times the respective light field mean wavelength;

positioning sample within said overlap volume;

generating a signal light field within said sample by the interaction of said light fields;

resolving the angular variation of said signal light emission from said sample in two-dimensions with at least one focusing optical component and a two-dimensional light detector array by arranging the optical separation of said focusing component from said light detector to be equal to said focusing component focal length;

measuring said angular variation of signal light in two-dimensions, identifying the occurrence or the lack of occurrence of coherently coupled quantum transitions or energy transfer within said sample thereby.

18. A method according to claim 16 or claim 17, wherein said method includes the step of positioning said focusing optical component with an optical separation of one focal length from said sample, for transforming said signal field in said sample to a corresponding optical far-field variation thereby.

19. A method according to claim 16 or claim 17, wherein said method further includes one of spectral filtering and spectral angular dispersing of said signal field, for modifying the signal light detected.

* * * * *